United States Patent [19]
Bedingham

[11] Patent Number: 5,335,658
[45] Date of Patent: Aug. 9, 1994

[54] INTRAVASCULAR BLOOD PARAMETER SENSING SYSTEM

[75] Inventor: William Bedingham, Maplewood, Minn.

[73] Assignee: Minnesota Mining and Manufacturing Company, St. Paul, Minn.

[21] Appl. No.: 906,740

[22] Filed: Jun. 29, 1992

[51] Int. Cl.⁵ .............................................. A61B 5/14
[52] U.S. Cl. .................................. 128/632; 128/634; 604/44
[58] Field of Search ............... 128/637, 632, 634, 692, 128/630, 633, 665, 635; 604/236, 43, 44

[56]   References Cited
U.S. PATENT DOCUMENTS

| | | |
|---|---|---|
| Re. 31,879 | 5/1985 | Lubbers et al. . |
| 2,629,399 | 2/1953 | Kulick . |
| 3,433,935 | 3/1969 | Sherman . |
| 3,461,856 | 8/1969 | Polanyi . |
| 3,498,286 | 3/1970 | Polanyi et al. . |
| 3,512,517 | 5/1970 | Kadish et al. . |
| 3,529,591 | 5/1968 | Schuette . |
| 3,612,866 | 10/1971 | Stevens . |
| 3,616,409 | 6/1968 | Tosteson . |
| 3,658,053 | 4/1972 | Fergusson et al. . |
| 3,674,013 | 4/1972 | Polanyi . |
| 3,807,390 | 4/1974 | Ostrowski et al. . |
| 3,814,081 | 6/1974 | Mori . |
| 3,841,308 | 10/1974 | Tate . |
| 3,866,599 | 2/1975 | Johnson . |
| 3,878,830 | 4/1975 | Bicher . |
| 3,893,448 | 7/1975 | Brantigan . |
| 3,983,864 | 10/1976 | Sielaff . |
| 4,008,717 | 2/1977 | Kowarski . |
| 4,016,864 | 4/1977 | Sielaff . |
| 4,050,450 | 9/1977 | Polanyi . |
| 4,073,297 | 2/1978 | Kopp . |
| 4,120,292 | 10/1978 | Le Blanc, Jr. et al. . |
| 4,187,856 | 2/1980 | Hall et al. . |
| 4,200,110 | 4/1980 | Peterson et al. . |

(List continued on next page.)

FOREIGN PATENT DOCUMENTS

| | | |
|---|---|---|
| 0273258 | 9/1987 | European Pat. Off. . |
| 0276977 | 1/1988 | European Pat. Off. . |
| 2215984 | 10/1972 | Fed. Rep. of Germany . |
| WO8401109 | 9/1983 | PCT Int'l Appl. . |
| 1593270 | 7/1981 | United Kingdom . |

OTHER PUBLICATIONS

IEEE Transactions on Biomedical Engineering, vol. BME-33, No. 2, Feb. 1986, pp. 117-132, IEEE, New York; J. L. Gehrich et al; "Optical fluorescence and its application to an intravascular blood gas monitoring system".

*Primary Examiner*—Lee S. Cohen
*Assistant Examiner*—Brian M. Green
*Attorney, Agent, or Firm*—Gary L. Griswold; Walter N. Kirn; Dale E. Hulse

[57]   ABSTRACT

A parameter of blood is sensed in vivo with a system which includes a catheter and a probe. The catheter has a lumen extending therethrough, a proximal end, a distal end and a distal opening at the distal end. The probe includes one or more sensing elements at its distal end. In one embodiment, the sensing element or elements are located at least about 4 mm proximal of the distal opening of the lumen. A volume oscillator is provided to control the movement of blood into and out of the lumen. A flush solution is introduced into the lumen so that when the volume oscillator is inactive the sensing element or elements are exposed to pure flush solution, which preferably includes an anti-clotting component. The probe is received within the catheter and affixed thereto. The volume oscillator is activated to move blood into and out of the lumen to expose the sensing element or elements to blood so that they can sense the blood parameter or parameters of interest.

35 Claims, 4 Drawing Sheets

U.S. PATENT DOCUMENTS

| | | |
|---|---|---|
| 4,535,786 | 8/1985 | Kater . |
| 4,201,222 | 5/1980 | Haase . |
| 4,210,029 | 7/1980 | Porter . |
| 4,265,249 | 5/1981 | Schindler . |
| 4,274,417 | 6/1981 | Delpy . |
| 4,295,470 | 10/1981 | Shaw . |
| 4,311,137 | 1/1982 | Gerard . |
| 4,322,164 | 3/1982 | Shaw et al. . |
| 4,340,615 | 7/1982 | Goodwin et al. . |
| 4,398,542 | 8/1983 | Cunningham et al. . |
| 4,407,290 | 10/1983 | Wilbur . |
| 4,444,198 | 4/1984 | Petre . |
| 4,471,765 | 9/1984 | Strauss . |
| 4,476,870 | 10/1984 | Peterson et al. . |
| 4,476,877 | 10/1984 | Barker . |
| 4,478,222 | 10/1984 | Koning et al. . |
| 4,502,488 | 3/1985 | Degironimo et al. . |
| 4,508,123 | 4/1985 | Wyatt et al. . |
| 4,543,961 | 10/1985 | Brown . |
| 4,557,900 | 12/1985 | Heitzmann . |
| 4,573,968 | 3/1986 | Parker . |
| 4,585,007 | 3/1986 | Uchigaki et al. . |
| 4,601,706 | 7/1986 | Aillon . |
| 4,608,996 | 9/1986 | Brown et al. . |
| 4,622,974 | 11/1986 | Coleman et al. . |
| 4,640,820 | 2/1987 | Cooper . |
| 4,651,741 | 3/1987 | Passafaro . |
| 4,684,245 | 8/1987 | Goldring . |
| 4,718,423 | 1/1988 | Willis et al. . |
| 4,736,748 | 3/1988 | Nakamura et al. . |
| 4,738,265 | 4/1988 | Ritchart et al. . |
| 4,774,955 | 10/1988 | Jones . |
| 4,785,814 | 11/1988 | Kane . |
| 4,810,655 | 3/1989 | Khalil et al. . |
| 4,830,013 | 5/1989 | Maxwell . |
| 4,951,669 | 8/1990 | Maxwell et al. . |
| 4,989,606 | 2/1991 | Gehrich et al. . |

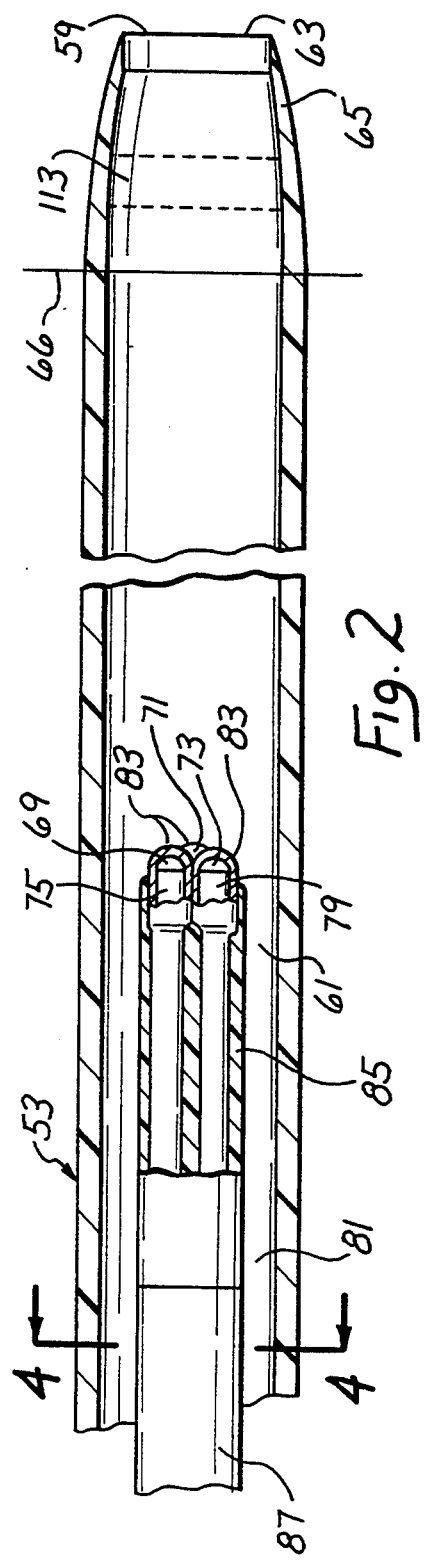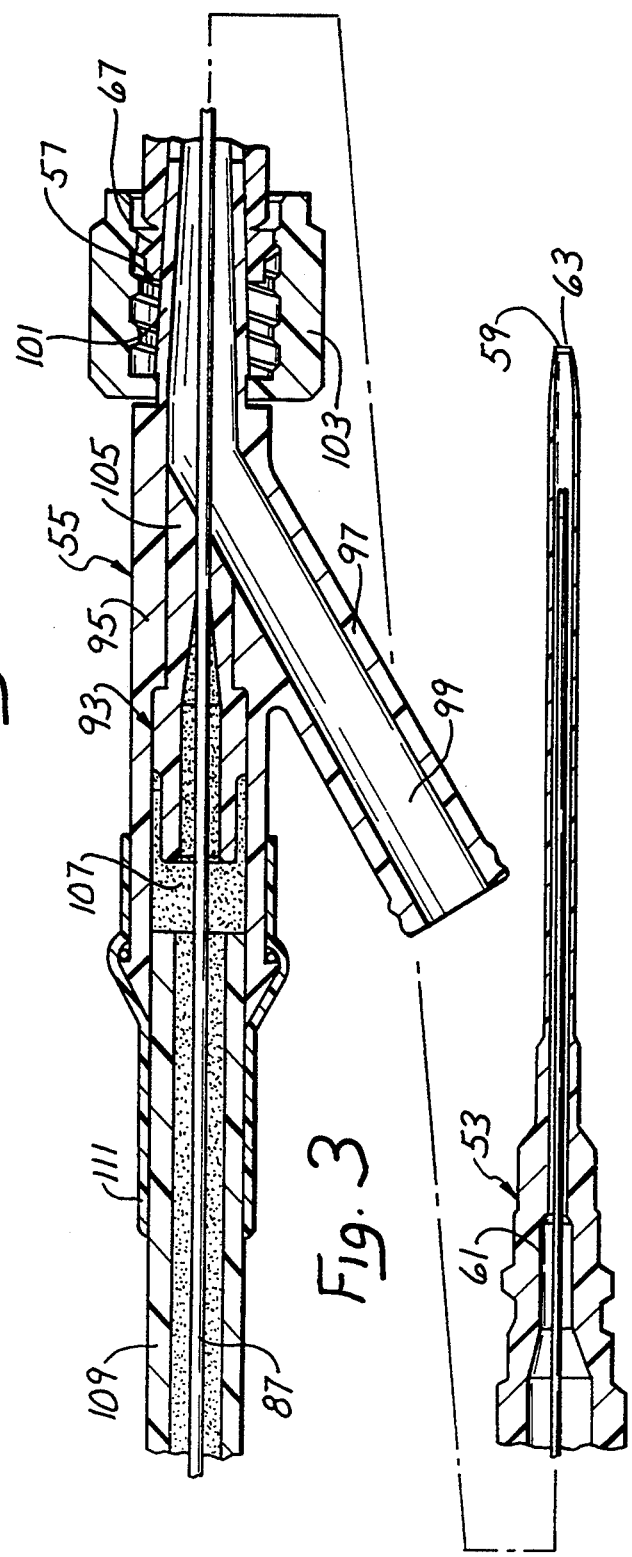

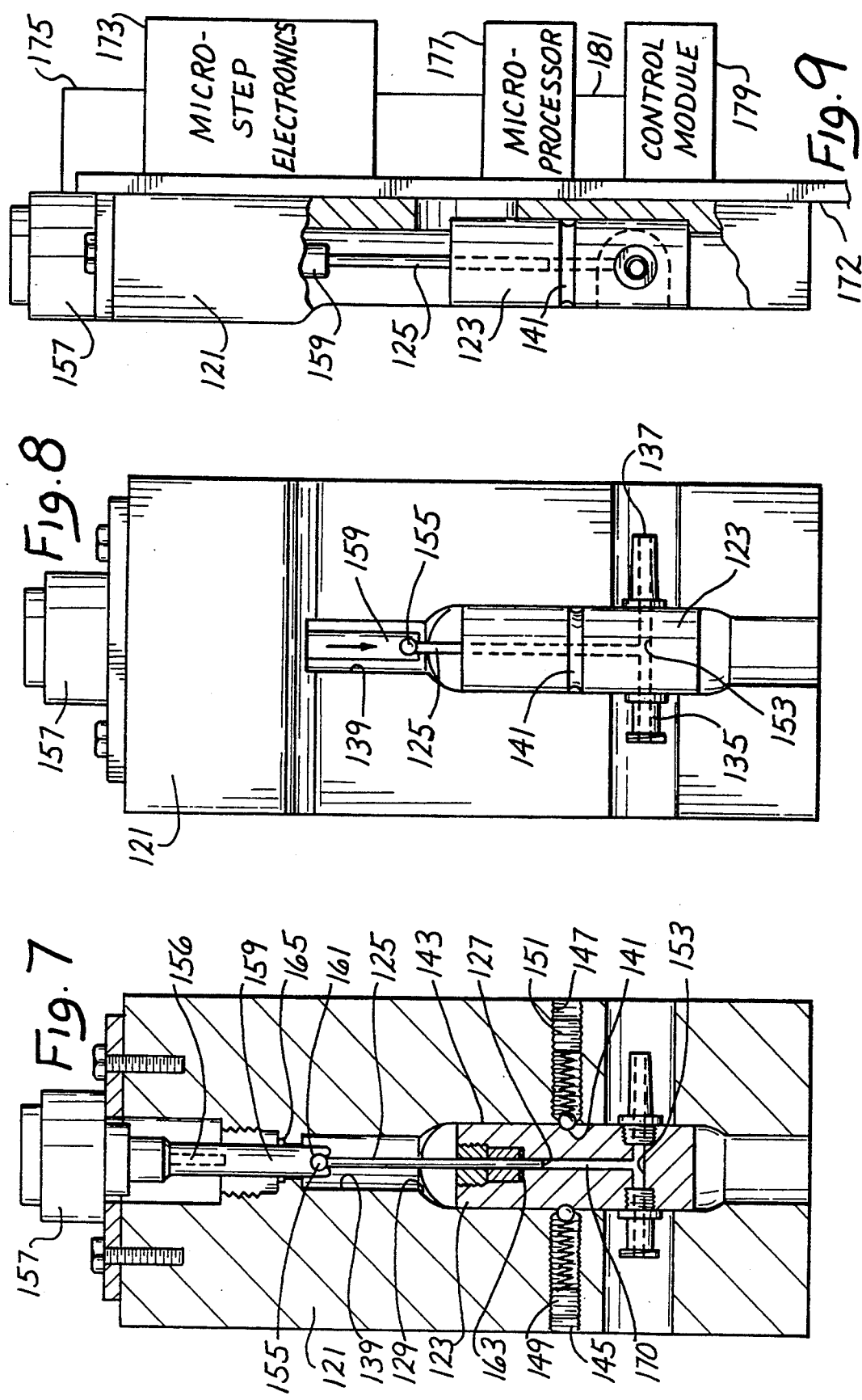

INTRAVASCULAR BLOOD PARAMETER SENSING SYSTEM

BACKGROUND OF THE INVENTION

The present invention relates to systems for sensing or measuring one or more parameters of blood from a blood vessel of a patient. More particularly, this invention relates to assemblies and methods useful for sensing a parameter of blood in vivo involving a catheter and a sensor probe a portion of which is located in a lumen of the catheter.

Sensors and sensor probes are well known, for example, for use in determining the concentrations (meaning to include therein the partial pressures of gases) of blood analytes or constituents of interest. Typically of interest is the determination of the concentration of gases, such as oxygen and carbon dioxide, of hydrogen ions (pH), of other electrolytes, of glucose and the like in the blood. These provide useful parameters for assessment of certain physiological conditions of a mammal, for example, a human medical patient.

Such sensors and sensor probes can be made sufficiently small in size to be used directly in vivo in a patient. This contributes to monitoring the condition of the patient on a continuous basis as opposed to older known procedures which require the extraction of a blood sample for determination in a remote laboratory of the constituents of interest in the blood.

An example of a useful blood sensor involves an optical indicator, such as a fluorescence indicator, located in association with a matrix material, such as a polymeric matrix material, on the optical face or surface of an optical fiber. Typically, a matrix material containing a fluorescent dye is loaded onto the optical surface of an optical fiber. Interaction of the dye with the component of interest, that is the component to be sensed, is monitored using optical signals carried by the optical fibers.

Maxwell U.S. Pat. No. 4,830,013 discloses in vivo sensing of various blood parameters using a sensor probe which is adapted to be inserted through a catheter into the cardiovascular system of a patient. A sensor probe is provided and preferably includes a plurality of sensors, each of which includes a sensor element adapted for sensing a parameter of blood and for providing a signal in response thereto and elongated transmission means, for example, an optical fiber, for transmitting the signal from the sensor element proximally.

The above-noted Maxwell patent discloses that the sensor is placed between 0.005 inch and 0.125 inch proximal of the distal opening of the lumen. An anti-clotting solution is provided through the lumen of the catheter to the patient. The combination of this solution and blood in the lumen creates an interface zone including both blood and anti-clotting solution. This interface zone is moved over the sensor so that the sensor can be bathed in blood for a period of time sufficient to enable the sensor to provide a signal relating to the blood parameter of interest, and to allow the anti-clotting solution to be expelled from the distal opening of the lumen. Thus, the sensor is either exposed to substantially exclusively blood or to a combination of blood and anti-clotting solution in the interface zone.

A related system is disclosed in Maxwell et al U.S. Pat. No. 4,951,669 in which the sensors are located in the fitting proximal of the catheter. In one embodiment, the sensors are shown in the lumen near the enlarged proximal end of the catheter. This system, which can be operated very similarly to the system in the above-noted Maxwell patent, is designed to allow the use of bigger sensor elements. Both the above-noted Maxwell and Maxwell et al patents are incorporated in their entireties herein by reference.

Carbon dioxide and relatively high concentrations of oxygen are blood parameters which are quite difficult to measure accurately.

It clearly would be advantageous to provide blood parameter sensing systems which provide enhanced accuracy.

SUMMARY OF THE INVENTION

New assemblies and methods for sensing parameters of blood have been discovered. The present invention is based, in part, on the discovery that the location of the sensor (sensing element) in the catheter is important to control the environment to which the sensor is exposed. By controlling this environment, it has been found that the accuracy of the blood parameter measurements obtained is benefitted. Moreover, substantial additional advantages, for example, in terms of ease of calibration and reduced thrombus formation, are achieved. Further, a new volume oscillator is provided which very effectively and efficiently controls the movement of blood into and out of the catheter. Blood is moved, preferably in a predetermined time sequence, by the volume oscillator to at least facilitate obtaining certain advantages achieved by the present system. Also, the volume oscillator is preferably structured to obtain added advantages, such as safety, disposability, predictability, cost effectiveness and reduced interference with other parts of the system. In short, the present systems effectively and efficiently provide accurate measurements of blood parameters.

In one broad aspect, the present invention is directed to assemblies for sensing blood parameters which comprise a probe and a catheter. The probe includes a sensing element for sensing a parameter of blood and for providing a signal in response to the sensed parameter, and an elongated transmission member for transmitting the signal from the sensing element. The catheter includes a lumen in which the sensing element is located. The lumen has an opening in the distal end. The catheter is sized and adapted so that at least the distal end and the opening in the distal end are receivable within a blood vessel of a patient.

In one embodiment, the sensing element is located in the lumen, for example, away from the proximal end of the catheter and/or closer to the distal opening than to the proximal end of the catheter, and at least about 4 mm, preferably at least about 6 mm, proximal of the distal opening. The sensing element is preferably located up to about 40 mm, more preferably up to about 20 mm, proximal of the distal opening of the lumen. By fixing the location of the sensing element as noted above, it has been found that the environment to which the sensing element is exposed can be controlled substantially independently of the tidal action caused by the heartbeat of the patient, and that only a relatively small amount of blood need be moved from the blood vessel of the patient into the catheter to expose the sensing element to substantially exclusively blood, for example, pure blood. Substantially independent control of the environment to which the sensing element is exposed facilitates the increased accuracy of the present system relative to, for example, the above-noted Maxwell system in which the heartbeat induced tidal action acted to move the blood back and forth over the sensors. As is disclosed hereinafter, the present system advantageously reduces the risks of blood stagnation and/or thrombus formation.

As used herein, the term "substantially exclusively" refers to a medium which effectively has the same average value of the parameter of interest as the pure medium. Thus, "substantially exclusively blood" is pure blood which may include another component, e.g., flush or drip solution, in an amount which is not effective to change the measured average value of the parameter of interest relative to the measured value of the parameter of interest in pure blood.

The movement of blood into and out of the lumen of the catheter is preferably controlled substantially solely by a volume oscillator in fluid communication with the lumen of the catheter. Thus, when the volume oscillator is inactive, the position of the sensing element in the lumen is such that the heartbeat of the patient, the size of the blood vessel in which the catheter is located, the compliance of the present system (other than the compliance provided by the volume oscillator itself), and all other environmental factors are insufficient to cause blood from the blood vessel of the patient to reach the sensing element. With the volume oscillator inactive, the sensing element is preferably exposed to substantially exclusively flush solution which passes through the lumen and into the blood vessel of the patient, at a relatively low rate, to keep the lumen patent. In other words, with the volume oscillator inactive, the sensing element is preferably removed or separated from both pure blood and the blood/flush solution interface zone.

In one embodiment, the sensing element is located so as to be exposed to or in substantially exclusively a non-blood-containing fluid medium, for example, the above-noted flush solution, during a portion of the time the sensing element provides the parameter sensitive signal. It has been found that monitoring the parameter sensitive signal even while the sensing element is located in substantially exclusively a non-blood-containing fluid medium unexpectedly provides improved accuracy for at least certain of the blood parameters in question, for example, the carbon dioxide concentration of the blood and for relatively high oxygen concentrations, for example, oxygen partial pressures of about 90 mm Hg or higher, of the blood. Thus, the sensing element provides a signal when the sensing element is exposed to substantially exclusively blood and when the sensing element is exposed substantially exclusively to a non-blood-containing fluid medium. Preferably, the time during which the sensing element is in or exposed to the blood/flush solution interface zone is reduced, more preferably minimized. It has been found that the value of the parameter of interest in the non-blood-containing fluid medium is often known and, therefore, can be accounted for relatively easily. The value of the parameter of interest in the interface zone is often ambiguous and variable, and is not easily accounted for. By reducing or minimizing the time during which the sensing element is exposed to this ambiguous interface zone, the accuracy of the measurement of the parameter of interest in pure blood can be increased.

The pure blood parameter value is obtained by monitoring the value of the parameter of interest when the sensing element is exposed to both substantially exclusively blood and substantially exclusively non-blood-containing fluid medium having a known value of the parameter so as to provide an average parameter value. The contribution to this monitored average value provided by the substantially exclusively non-blood-containing fluid medium is then factored out to arrive at the value of the parameter in pure blood. This approach provides pure blood parameter values which are more accurate than values obtained while the sensing element (during the time a parameter sensitive signal is being provided) is exposed only to substantially exclusively blood and the blood/flush solution interface zone.

Having the sensing element located as described herein provides one or more additional substantial advantages. For example, the sensing element can be easily calibrated using a one point system, that is calibrating the sensing element based upon the known volume of the parameter of interest in the non-blood-containing fluid medium, e.g., pure flush solution. Since, with the volume oscillator inactive, the sensing element is preferably exposed substantially exclusively to the flush solution, which preferably includes an anti-clotting component such as heparin, the tendency to thrombus formation at or near the distal tip of the probe is reduced. In addition, because pure blood and the blood/flush solution interface zone are located outside the lumen or very near the distal end of the lumen when the volume oscillator is inactive, the tendency for blood to stagnate in the lumen is also reduced. Moreover, when the volume oscillator is activated, it is possible to "wash" or "flush" the sensing element with the flush solution periodically. This again reduces the tendency to thrombus formation.

In another broad aspect of the present invention, volume oscillators which are adapted to be placed in fluid communication with a lumen of a catheter, for example, as described above, are provided. These volume oscillators are positioned so as to control the flow of blood from a blood vessel of a patient into and out of the lumen. In one embodiment, such volume oscillators comprise a housing defining a fluid flow path, a piston moveable relative to the housing and together with the housing defining a chamber of variable volume, a stem secured to the piston and adapted to be activated to move the piston relative to the housing to vary the volume of the chamber, and an actuator adapted to be removeably coupled to the stem and to activate the stem.

Preferably, the stem is activated in a predetermined time sequence so that the volume of the chamber varies with time in accordance with a wave form other than a simple sine wave. Previous systems have employed a simple sine wave form to control the movement of a piston. However, such a simple sine wave form provides that the sensing element is exposed to substantially exclusively blood for only a relatively small fraction of the total time the volume oscillator is activated or requires that a relatively large amount of blood be moved into and out of the lumen. This sine wave activation of the volume oscillator also exposes the sensing element to the ambiguous blood/flush solution interface zone for a relatively large fraction of the time the volume oscillator is activated. The present volume oscillator is more preferably activated in accordance with a wave form so that the fraction of the total time the volume oscillator is active during which the sensing element is exposed to substantially exclusively blood is increased and/or the fraction of the total time the volume oscillator is active during which sensing element is exposed to the blood/flush solution interface zone is decreased, relative to the volume oscillator being activated in accordance with a simple sine wave.

A particularly useful class of wave forms are those which provide that the amount of blood in the lumen of the catheter is maintained substantially constant for a portion, more preferably a major portion, of the time the volume oscillator is activated. Such wave forms reduce, and even eliminate, any interference caused by the action of the volume oscillator on the measurement of the patient's blood pressure through the lumen. A true and accurate blood pressure can be measured through the lumen with the volume oscillator activated when the amount of blood in the lumen is maintained substantially constant.

In one embodiment, the housing, piston and stem are adapted to be disposed of after use with a single patient. In this manner, improved patient safety is achieved. Also, since the actuator is adapted to be removeably secured to the stem, it can be repeatedly used. The actuator often includes the more costly components of the present volume oscillator assemblies. Therefore, by disposing of certain components which may be exposed to blood after a single use while repeatedly using other, more costly components, the present volume oscillators provide for patient safety and isolation in a cost effective manner.

The actuator preferably includes a motor with a motor shaft which is adapted to be removeably coupled to the stem. A control system is provided which is adapted and positioned to provide control information to the motor to control the motor and thereby control the time sequence in which the stem is activated. This control system preferably includes a microprocessor which is adapted to be preprogrammed to provide the control information.

In one particularly useful embodiment, the present volume oscillator assemblies further comprise a holder sized and adapted to carry the housing and at least a portion of the actuator, for example, the motor. This holder, which preferably is used repeatedly (and not disposed of after use with a single patient), includes a cavity sized and adapted to receive and hold the housing. The holder and housing include positioning elements which are adapted to be mutually engaged to hold the housing in the cavity. In this manner, the disposable components of the present system can be placed in and removeably secured to the holder for use. After use, the disposable components of the present assemblies are removed, suitably disposed of, and replaced by a new disposable sub-assembly for use with the same patient or a different patient.

Methods for sensing a parameter of blood are provided. In one embodiment, these methods comprise providing a catheter, such as described herein, with the distal opening being positioned within the blood vessel of a patient. A probe, such as described herein, is provided at least partially within the lumen of the catheter so that the sensing element is located as described herein. A flush, e.g., drip, solution from a flush solution source is introduced into the lumen. A volume oscillator which, when activated, moves blood from the blood vessel of the patient into and out of the lumen is provided. A signal responsive to the parameter of interest is obtained from the sensing element while the sensing element is exposed to substantially exclusively blood. The volume oscillator preferably acts to provide that the sensing element is exposed to substantially exclusively blood for a major portion of the time the volume oscillator is activated. In a particularly useful embodiment, the sensing element is exposed to substantially exclusively the flush solution for another portion of the time the volume oscillator is activated. In this embodiment, the parameter sensitive signal is preferably also obtained while the sensing element is exposed to substantially exclusively the flush solution.

The probe may carry one or more sensing elements depending upon the number of parameters of interest. These sensing elements can be of any type, such as electro-chemical, that is suitable for sensing the parameter of interest; however, optical sensing elements are preferred, and fluorescent sensing elements are considered optimum. Although multiple sensing elements could be provided to sense the same blood parameter, preferably, each sensing element senses a different blood parameter. In a preferred construction, the transmission member includes an optical fiber for each of the sensing elements, with the sensing element being located on the distal end of the associated optical fiber. The sensing elements provide signals related to the associated blood parameters of interest, and such signals may be used or processed continuously, intermittently or on demand, preferably continuously while the volume oscillator is activated, to provide readings indicative of the blood parameters of interest.

The invention, together with additional features and advantages thereof, may best be understood by reference to the following description taken in connection with the accompanying illustrative drawings.

BRIEF DESCRIPTION OF THE DRAWINGS

FIG. 2 is an enlarged fragmentary sectional view of the distal region of one form of probe and catheter usable in the assembly of FIG. 1.

FIG. 3 is a longitudinal sectional view through the probe-catheter assembly.

FIG. 7 is a cross-sectional view of the volume oscillator showing the piston stem in a substantially fully extended position.

FIG. 8 is a front plan view of the volume oscillator showing the piston stem in a substantially fully retracted position.

FIG. 9. is a side view, partly in cross-section, of the volume oscillator.

DETAILED DESCRIPTION OF THE DRAWINGS

Figure 1:
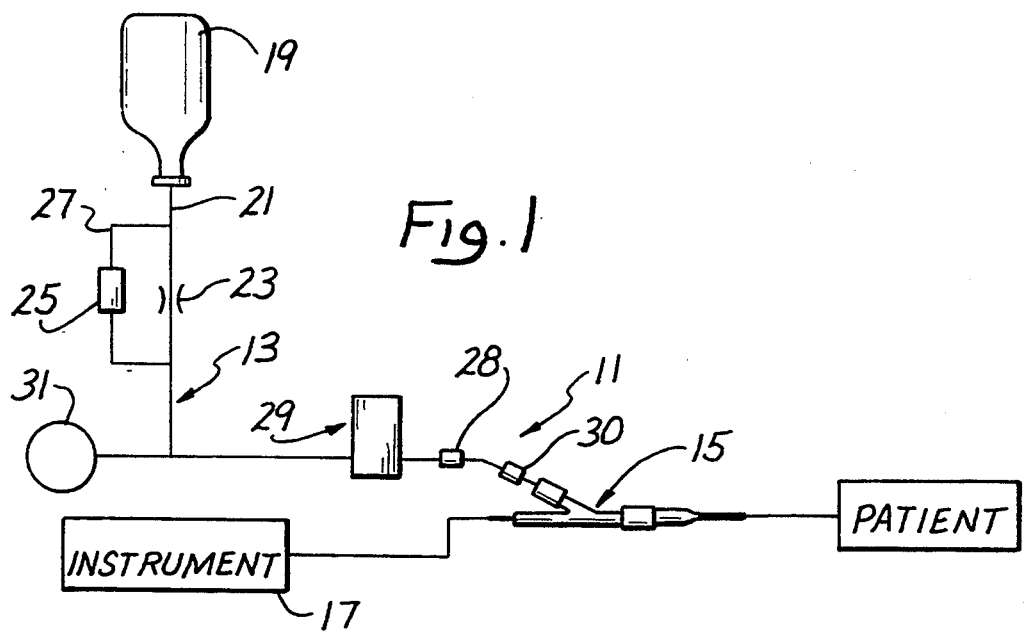
FIG. 1 is a schematic view of an assembly for the in vivo measurement of blood parameters of interest.

FIG. 1 shows an assembly 11 for the in vivo measurement of various blood parameters, and particularly the pH value and the concentrations (partial pressures) of oxygen and carbon dioxide. Although the assembly 11 can be of different constructions, in this embodiment it includes a solution introducing system 13 and a probe-catheter assembly 15. The assembly 11 may also include an instrument 17 for providing a readout of the blood parameters of interest.

Generally, the solution introducing system 13 introduces an appropriate anti-clotting solution, such as a heparinized saline solution, through the probe-catheter assembly 15 to the patient to keep the line leading to the patient patent. Although this can be accomplished in different ways, in the embodiment shown schematically in FIG. 1, the system 13 includes a pressurized source 19 of heparinized saline solution, a conduit 21 leading from the source to the probe-catheter assembly 15, a flow restrictor 23 to reduce the rate of flow through the conduit 21 to the desired drop rate, a flush valve 25 in a bypass 27 around the restrictor 23, a stop cock 28, a volume oscillator, shown generally at 29, a blood withdrawal site 30 and a pressure transducer 31. Except as noted elsewhere herein, all of the components of the system 13 may be conventional, and the system 13 may include other components, if desired. In the illustrated embodiment, solution from the pressurized source 19 flows through the restrictor 23 at a relatively slow rate, such as 2 to 4 ml/hour. The solution flows through the volume oscillator 29 and the probe-catheter assembly 15 to the patient. If a more rapid flow rate from the source 19 is desired, as for example during priming, the flush valve 25 can be manually opened to provide a relatively high-rate flow path around the restrictor 23 in a conventional manner.

The pressure transducer 31 communicates with the conduit 21 and can measure the pressure therein. Accordingly, with the probe-catheter assembly 15 inserted into the vascular system of a patient, the pressure transducer 31 can provide blood pressure readings. Volume oscillator 29 is structured and operates, as discussed in detail hereinafter, to have little or no detrimental effect on the blood pressure readings provided by pressure transducer 31. The blood withdrawal site 30 is used for taking blood samples from the patient through the probe-catheter assembly 15. The stop cock 28 is located proximally of the site 30 so that, by closing the stop cock 28, the flush solution in the conduit 21 cannot be withdrawn during a blood withdrawal procedure.

The probe-catheter assembly 15 includes a catheter 53 and a probe 55 (FIG. 3). The catheter 53 may be a conventional arterial catheter. As such, the catheter 53 may include a proximal end 57, a distal end 59, a lumen 61 extending axially, completely through the catheter and opening at a distal opening 63 at the distal end. The catheter 53 has a standard lead-in taper, i.e., a tapered zone 65, which extends from a reference plane 66 along the outer periphery of the catheter 53 to the distal end 59. The diameter of the lumen 61 also decreases distally throughout the tapered zone 65 as shown in FIG. 2. The catheter 53 has an externally threaded coupling 67 at its proximal end.

Figure 4:
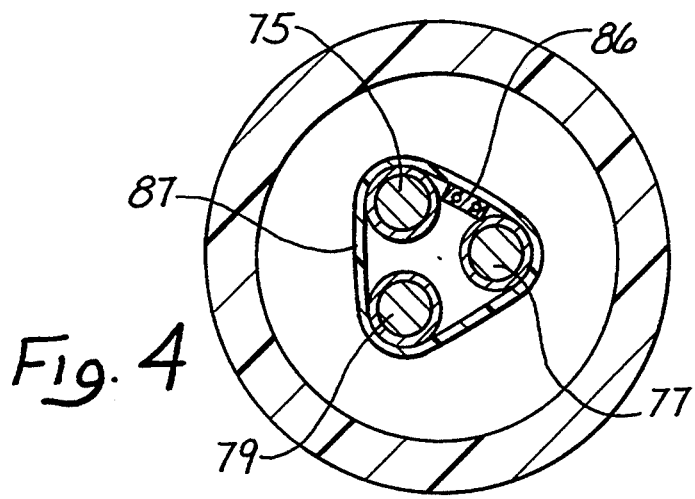
FIG. 4 is an enlarged sectional view taken generally along line 4—4 of FIG. 2.
Figure 6:
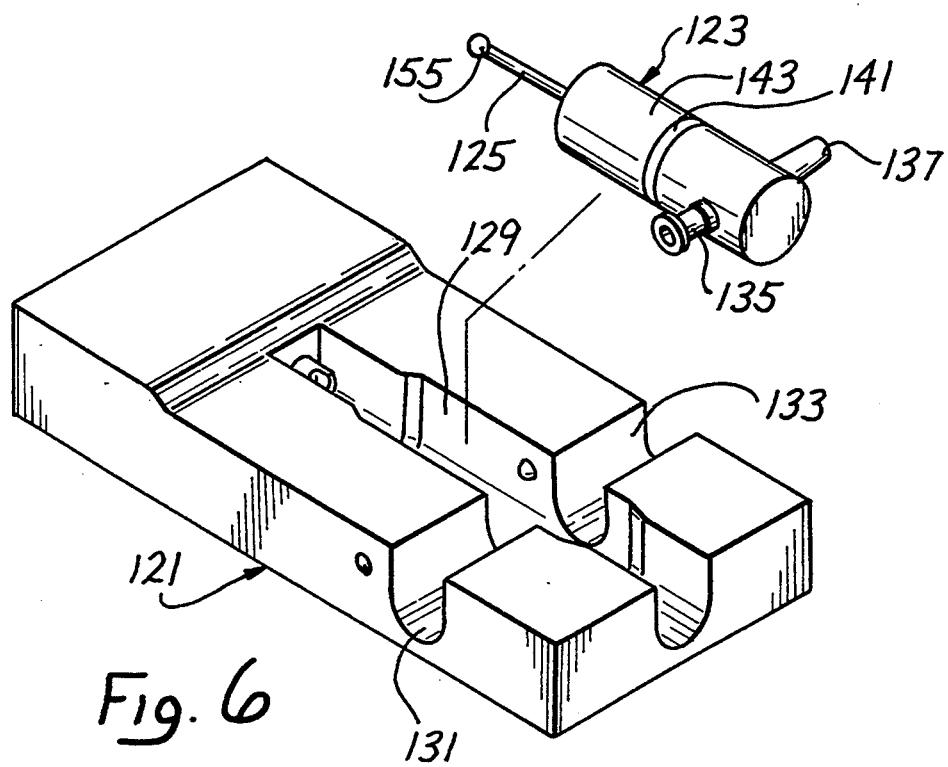
FIG. 6 is a perspective view of certain disassembled components of the volume oscillator.

The probe 55 may be of various different constructions. In the embodiment illustrated, probe 55 includes an oxygen sensor 69, a carbon dioxide sensor 71 and a pH sensor 73, with each of the sensors or sensing elements affixed to the distal ends (optical surfaces) of single optical fibers 75, 77, and 79, respectively (FIG. 4). In this embodiment, the sensors 69, 71 and 73 are fluorescent optical sensors, and they respond to the concentration of oxygen, the concentration of carbon dioxide and the pH value, respectively, to provide continuous optical signals indicative of the condition sensed. The optical fibers 75, 77 and 79 serve as transmission members for transmitting the signals from the associated sensors proximally. The probe 55 has a very small cross-sectional area. For example, the average transverse dimension, or diameter, of the probe 55 within the lumen 61 perpendicular to the longitudinal axis of the probe is preferably about 0.56 mm or less so that it fits within the lumen with an ample radial clearance 81 as shown in FIG. 2. A probe having the specific small size noted above is particularly useful when it is to be placed in a conventional 20 gauge intra-arterial catheter, such as a 20G Deseret Insyte polyurethane catheter. Both the surface of the catheter 53 and the portion of the probe 55 within the lumen 61 may be coated or otherwise associated with heparin or the like anti-clotting component. The present system reduces the risks of thrombus and clot formation so that excellent results, for example, in terms of sensing accuracy and biocompatibility, are achieved without so treating such surfaces, in particular the catheter surface, with such anti-clotting component.

The sensors or sensing elements 69, 71 and 73 are each located away from the proximal end 57 of catheter 53, about 6 mm proximal of the distal opening 63 of the lumen 61. By locating the sensors 69, 71 and 73 in this manner it has been found that, with volume oscillator 29 inactive, the sensors are exposed substantially exclusively to flush solution even in the "worst" case in which the patient's heartbeat and other environmental factors combine to cause blood from a human patient's blood vessel to enter the opening and extend proximally into lumen 61. Also, with the sensors 69, 71 and 73 positioned in this manner, volume oscillator 29 controls completely the time sequence in which blood is exposed to the sensors. It should be noted that with larger catheters, the sensing elements can be located somewhat more distally and still achieve certain of the benefits of the present invention. For example, with a conventional 18 gauge catheter, the sensing elements can be located within about 2.4 mm of the distal opening of the lumen. To reduce the risk of blood stagnation and thrombus formation, it is preferred that the sensing elements 69, 71 and 73 be located away from the proximal end 57 of catheter 53, more preferably at least about 10 mm distal of the proximal end of the catheter.

The volume oscillator 29 can be preprogrammed with a wave form, preferably other than a simple sine wave, which controls the time sequence in which the sensors 69, 71 and 73 are exposed to substantially exclusively blood, and to substantially exclusively flush solution. This control, which is substantially independent of the heartbeat of the patient in whose cardiovascular system catheter 53 is located and of all other components of assembly 11, is an important aspect of the present invention and facilitates obtaining accurate blood parameter measurements.

The particular design of the probe 55 forms no part of this invention because this invention is applicable to probes of various different constructions. Briefly, however, the sensors 69, 71 and 73 are attached to the distal ends of the associated optical fibers 75, 77 and 79 in any suitable manner, and each of the sensors and the associated fiber is separately encased in an inner overcoat 83 which, among other things, may assist in retaining the sensor on the end of the associated fiber. The overcoat 83 is, of course, permeable to the relevant blood parameters so that such parameter, or one related to it, can be sensed by the sensors. An outer overcoat 85 covers the inner overcoats 83 and a length of the fibers just proximally of the overcoats 83. Outer covercoat 85 may, and preferably does, form a smooth distal tip of probe 55 which reduces the risk of thrombus formation. Proximally of the overcoat 85, the optical fibers 75, 77 and 79 and a temperature-sensitive element, such as a thermocouple 86 (FIG. 4), are suitably encased within an appropriate sheath 87.

The probe 55 includes a "Y" fitting 93 at its proximal end as shown in FIG. 3. The optical fibers 75, 77 and 79 extend within the sheath 87 completely through one leg 95 of the "Y" fitting 93 to the instrument 17, as shown in FIG. 1. Another leg 97 of the fitting 93 has a passage 99 which communicates with the lumen 61, and more particularly, with the clearance 81 around the probe 55. The leg 97 is coupled to the conduit 21 of the system 13 as shown in FIG. 1. A third leg 101 of the "y" fitting 93 carries a rotatable internally threaded coupling 103 for attaching the "y" fitting of the probe 55 to the proximal end 57 of the catheter 53 outside the cardiovascular system of the patient.

Although the details of the fitting 93 form no part of this invention, the sheath 87 may be guided in the leg 95 by a sleeve 105 and retained in position by potting 107. The sheath 87 extends within a flexible tube 109 suitably attached to the leg 95, and shrink tubing 111 is provided over the adjacent end portions of the fitting and the tube for strain relief.

With the proximal end 57 of the catheter 53 coupled to the probe 55 by the coupling 103, the distal portion of the probe is within the lumen 61, and the sensors 69, 71 and 73 are within the lumen properly positioned relative to the distal opening 63, as shown in FIG. 2. With the catheter 53 within the cardiovascular system of the patient, such as in a radial artery, the catheter keeps the sensors 69, 71 and 73 from contacting the wall of the artery.

Referring now to FIGS. 6 to 9, volume oscillator 29 includes a holder 121, a housing 123, a piston stem 125 and a piston end surface 127. Holder 121 includes a centrally located longitudinal cavity 129 which is sized and adapted to receive housing 123, and laterally extending cavities 131 and 133 sized and adapted to receive first extension 135 and second extension 137, respectively, of the housing. Longitudinal cavity 129 includes an upwardly extending portion 139 adapted to accommodate the movement of piston stem 125 into and out of housing 123. Holder 121 may be made of any suitable material, such as a suitable polymeric material.

Housing 123 is adapted to be removeably secured to holder 121. Although various different constructions may be employed, the embodiment illustrated involves a peripheral groove or recess 141 in the cylindrically shaped sidewall 143 of housing 123. Holder 121 includes two threaded holes 145 and 147 which pass through holder 121 and terminate at cavity 129. Conventional spring/ball assemblies 149 and 151 are threaded into holes 145 and 147, respectively. The balls of these assemblies are biased to extend into cavity 129. Housing 123 can be placed in cavity 129 only by placing the balls of assemblies 149 and 151 into recess 141. The biasing of these balls holds housing 123 in place in cavity 129, as shown in FIG. 7. Housing 123 can be conveniently removed from holder 121 by manually overcoming this biasing.

Housing 123 defines a flow path 153 which extends through extensions 135 and 137 and provides fluid communication between conduit 21 and lumen 61. When volume oscillator 29 is inactive, piston end surface 127 is stationary relative to the housing 123 and preferably substantially flush with the wall of flow path 153 so that no flush solution accumulates in volume oscillator 29.

The enlarged end 155 of piston stem 125 opposite piston end surface 127 is adapted to be removeably secured or coupled to the shaft 156 of a stepping motor 157, which is carried by holder 121. Alternately, a proportional solenoid can be used in place of stepping motor 157. Although various different constructions may be employed, the embodiment illustrated includes a shaft extension 159 secured to shaft 156. Extension 159 includes an open ended socket-like element 161 sized and adapted to receive and hold the enlarged end 155 of piston stem 125. This coupling is secure during use of volume oscillator 29, but can be easily overcome by manual force when it is desired to remove housing 123 and piston stem 125 from holder 121. 0-ring seal 163 is positioned to keep the flow path 153 and chamber 170 hermetically sealed. 0-ring seal 165 is positioned so that any fluid spills are prevented from contacting the motor 157. Housing 123 and piston stem 125 are disposable, for example, after use with a single patient, while holder 121 (and the other components of volume oscillator 29) are used repeatedly with many patients. Since no blood comes into contact with the holder 121, there is no cross contamination between patients.

Housing 123 and piston end surface 127 together form an open ended generally cylindrically shaped chamber 170 the volume of which varies depending on the position of surface 127. When volume oscillator 29 is inactive, the volume of chamber 170 is substantially zero.

In the embodiment illustrated, as shown in FIG. 9, stepping motor 157 is directly secured to holder 121. Holder 121, in turn, is secured to a panel 172, which may be conveniently placed on a conventional IV pole placed beside the patient. The pressure transducer 31 may also be mounted on the panel 172.

Stepping motor 157 has a "keyed" lead screw to provide linear motion to the motor shaft 156, and normally operates so that the shaft moves in individual steps of a given magnitude. In order to reduce the effect that the volume oscillator 29 has on the other components of the system 11, and in particular on the blood pressure readings provided by pressure transducer 31, it is preferred that the stepping motor 157 be controlled so as to at least reduce the magnitude of these individual steps. More preferably, the motor 157 is controlled so that the motor shaft 156 moves substantially smoothly, that is substantially without taking individual steps.

The motor 157 is controlled by a system in which control information is imputed from a control module 179 to a microprocessor 177 which, in turn, processes this information in accordance with one or more relationships, e.g., a wave form through which the piston stem 125 is to be moved, previously programmed into the microprocessor. This processing results in control signals being passed from the microprocessor 177 to electronics 173, including, for example, digital/analog convertors, power amplifiers and related components, to control the action of the motor 157.

As shown in FIG. 9, such electronics 173, termed micro-step electronics to connote the "smoothing out" function of such electronics, are secured to panel 172 and are in electrical communication with stepping motor 157 through electrical conduit 175. Also secured to panel 172 is the microprocessor 177 and the control module 179.

Figure 5:
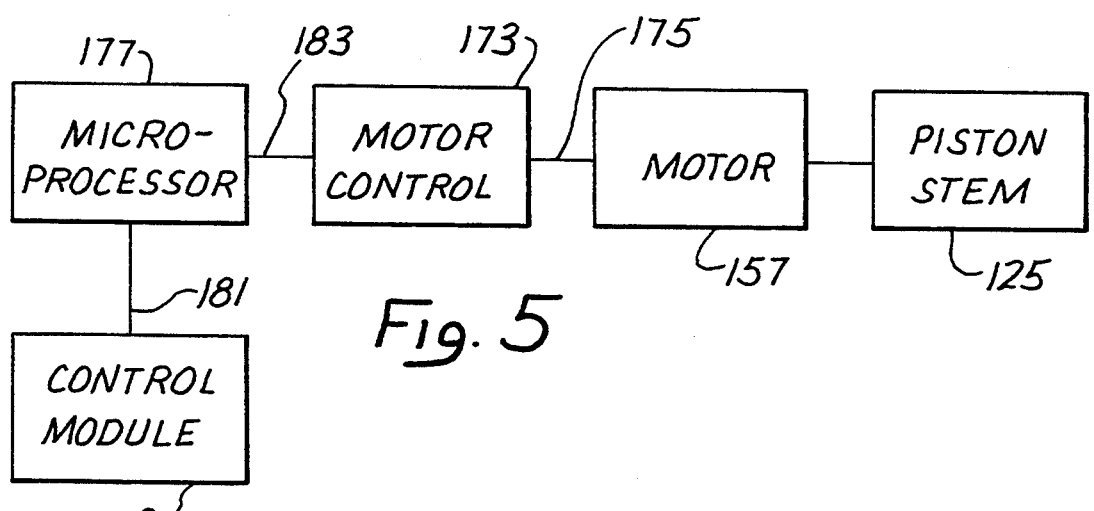
FIG. 5 is a generalized schematic illustration of the volume oscillator assembly employed in FIG. 1.

FIG. 5 schematically illustrates how the movement of piston stem 125 is controlled. Control module 179 is in electrical communication, through conduit 181, with microprocessor 177, which can be of conventional design. Information, for example, the amount of time the piston stem 125 is to take to move through one complete cycle (the cycle time) and whether the volume oscillator 29 is to be continuously or intermittently active, is manually imputed into microprocessor 177 through control module 179, for example, through a series of touch keys, switches and the like on the control module. Microprocessor 177 processes this input in accordance with one or more relationships, for example, the wave form through which piston stem 125 is to move in one complete cycle, previously programmed into the microprocessor. Control instructions, in the form of electrical signals, are then given by microprocessor 177 to motor control (or micro-step electronics) 173 through conduit 183 which, in turn, controls the action of motor 157 and the movement of piston stem 125.

The position of the piston stem 125 varies the volume of chamber 170 in accordance with a wave form, preferably other than a simple sine wave, which wave form is preprogrammed into the microprocessor 177, using conventional microprocessor programming techniques.

In use of the assembly 11, the catheter 53 is first inserted into the radial artery using conventional techniques. Next, the probe 55 is inserted into the lumen 61 and attached to the proximal end of the catheter 53 with the coupling 103. This properly positions the sensors 69, 71 and 73 within the lumen 61 about 6 mm from the distal opening 63. Conventional priming techniques may be employed to provide the desired controlled flow of the flush or drip solution from source 19 into the lumen 61.

With volume oscillator 29 inactive, the flush or drip solution from the source 19 completely fills the lumen 61 around the probe 55. The solution is provided under a pressure such that there is a slow flow of solution from the lumen 61 into the patient's artery. This introduction of the solution through the lumen 61 and into the artery results in an interface zone 113 adjacent the distal opening 63 which has some axial length and which includes both blood and the solution from the source 19. The interface zone 113 is a partition between substantially exclusively blood distally of the interface zone and substantially exclusively solution, e.g., anti-clotting solution, from source 19, proximally of the interface zone. One important feature of the present invention involves at least reducing, or even minimizing, the amount (or fraction) of time that the sensors are exposed to this interface zone 113 while the volume oscillator 29 is active, for example, relative to a volume oscillator which functions in accordance with a simple sine wave form. Also, in accordance with the present invention, the sensors 69, 71 and 73 are exposed to substantially exclusively solution from source 19 when the volume oscillator 29 is inactive.

with the volume oscillator 29 inactive, the interface zone 113 moves axially back and forth near the opening 63 of the lumen 61 in a tidal action as a result of the rising and falling of the patient's blood pressure with each heartbeat. However, with the volume oscillator 29 inactive, the interface zone 113 does not move sufficiently proximally of the opening 63 to contact the sensors 69, 71 and 73. Thus with the volume oscillator 29 inactive, the sensors 69, 71 and 73 are in substantially exclusively the solution from source 19. This reduces the risk of thrombus formation at the tip of the sensors. In addition, with the sensors 69, 71 and 73 located substantially exclusively in the solution from source 19, the sensors can be effectively calibrated. For example, the carbon dioxide concentration of a typical heparinized saline solution from source 19 is substantially zero. Thus, the carbon dioxide sensor 71 can be very effectively calibrated when the sensor is located in substantially exclusively the solution from source 19. Similar calibrations can be obtained for the oxygen sensor 69 and for the pH sensor 73 because the oxygen concentration and the pH of the solution from source 19 are known. Moveover, these calibrations can be routinely checked and rechecked when the sensors are exposed substantially exclusively to the solution from source 19, for example, when volume oscillator 29 is inactive.

In addition, with the volume oscillator 29 inactive, the pressure transducer 31 can very effectively monitor the blood pressure of the patient in whose cardiovascular system the catheter 53 is located.

Information is manually imputed through control module 179 to microprocessor 177 to control the activation of volume oscillator 29. Control module 179 may include one or more visual displays, for example, made up of liquid crystal displays, light emitting diodes and the like, which provide a visual display of one or more portions of the information, for example, the cycle time, imputed through the control module. As discussed above, microprocessor 177 processes this information in accordance with a preprogrammed wave form and provides instructions to electronics 173 to control the action of motor 157 and, thereby, the movement of piston stem 125.

When volume oscillator 29 is activated, piston stem 125 is caused to move in accordance with this imputed information and the preprogrammed wave form, which preferably is other than a simple sine wave. During at least one portion of the cycle or wave form through which the piston stem 125 moves, chamber 170 increases in size or volume so as to draw blood from the blood vessel of the patient back into the lumen 61 of catheter 53 so that the sensors 69, 71 and 73 are located in or exposed to substantially exclusively such blood. Preferably, when the volume oscillator 29 is activated, the sensors 69, 71 and 73 provide parameter sensitive signals to the instrument 17 so that values of the parameters of interest can be determined and monitored. Such signals are provided, preferably continuously provided, throughout the time the volume oscillator 29 is active. Such signals may also be provided during at least a portion of the time when the volume oscillator 29 is inactive.

It is preferred that the initial action of the piston stem 125 be such so as to draw blood relatively quickly into the lumen 61 so that the sensors 69, 71 and 73 are quickly exposed to substantially exclusively blood. This reduces, or even minimizes, the time during which the blood is exposed to the interface zone 113. The velocity at which blood is drawn into and expelled from the lumen 61 should be tempered or moderated so as to avoid damaging the blood itself. Since the system 11 may be employed for relatively long periods of time, for example, on the order of about 72 hours or longer, with blood being drawn into and expelled from the lumen 61 many times, it is important that the system have no substantial detrimental effect on the blood itself.

For an intermediate period of time during the movement cycle of the piston stem 125, the volume oscillator 29 preferably operates so as to maintain the sensors 69, 71 and 73 in substantially exclusively blood. During this time, because the drip solution is continuing to be pumped from source 19, the piston stem 125 may continue to be moved so as to increase the volume of chamber 170. This increase in volume of chamber 170 is preferably predetermined so as to accommodate the amount of solution from source 19 which would have flowed into lumen 61 during this period of time so that the blood level in the lumen is maintained substantially constant.

After this intermediate period of time, which preferably is at least a major portion and more preferably at least about 70%, of the total time required for a single cycle of the piston stem 125, the piston stem is preferably moved so as to push blood from the lumen 61 of the catheter 53 out through the distal opening 63. This movement is done relatively quickly. Again, care should be taken to avoid too rapid movement of blood through the distal opening 63 so as not to damage the blood. However, once substantially all the blood has been removed from the catheter 53, the rate of travel of the piston stem 125 is preferably increased so as to provide a fast or rapid flush of the tip of the sensors 69, 71 and 73 with the anti-clotting solution from source 19. This flushing action reduces the risk of thrombus formation at the tip of probe 55. At the end of this "flush" period, the cycle of the piston stem 125 is completed and the volume of chamber 170 is substantially zero. This cycle can be repeated, if desired.

It should be noted that the relatively rapid movement of blood into and out of the lumen 61 reduces, and even minimizes, the amount of time during which the sensors 69, 71 and 73 are exposed to the interface zone 113, which often has ambiguous and uncertain concentrations of the constituents of interest. In so doing, the amount of time during which the sensors 69, 71 and 73 are exposed to such ambiguous concentrations of the constituents of interest is reduced or minimized. This feature increases the accuracy of the present system.

Since the wave form used to move the piston stem 125 and the position of the sensors 69, 71 and 73 in lumen 61 are known, it is easily determined what fraction of the cycle time of the piston stem 125 that the sensors 69, 71 and 73 are exposed to substantially exclusively the solution from source 19. Thus, by factoring out this fraction of the cycle time multiplied by the concentration of the constituent of interest in the solution from source 19 (which is a known concentration) from the average value of the parameter of interest monitored by instrument 17 during the time volume oscillator 29 is activated, one can very conveniently and accurately determine the value of the parameter of interest in the blood in the radial artery of the patient.

Because the wave form of the movement of the piston stem 125 is preferably chosen so that when the sensors 69, 71 and 73 are located substantially exclusively in blood the level or the amount of blood in the catheter 155 is maintained substantially constant, the blood pressure readings monitored by the pressure transducer 31 during this period of time are substantially unaffected by the volume oscillator 29 even though the volume oscillator is active or activated. Thus, little or no interference with blood pressure monitoring results from the action of the volume oscillator 29.

The following non-limiting example illustrates certain aspects of the present invention.

EXAMPLE

The system 11 is operated to monitor the carbon dioxide, oxygen and pH levels of the blood in the radial artery of a patient. The catheter employed is a 20G Insyte catheter. The probe 55 has an average diameter of 0.51 mm. The rate at which heparinized saline solution from source 19 enters lumen 61 is 3.5 ml/hr.

Figure 10:
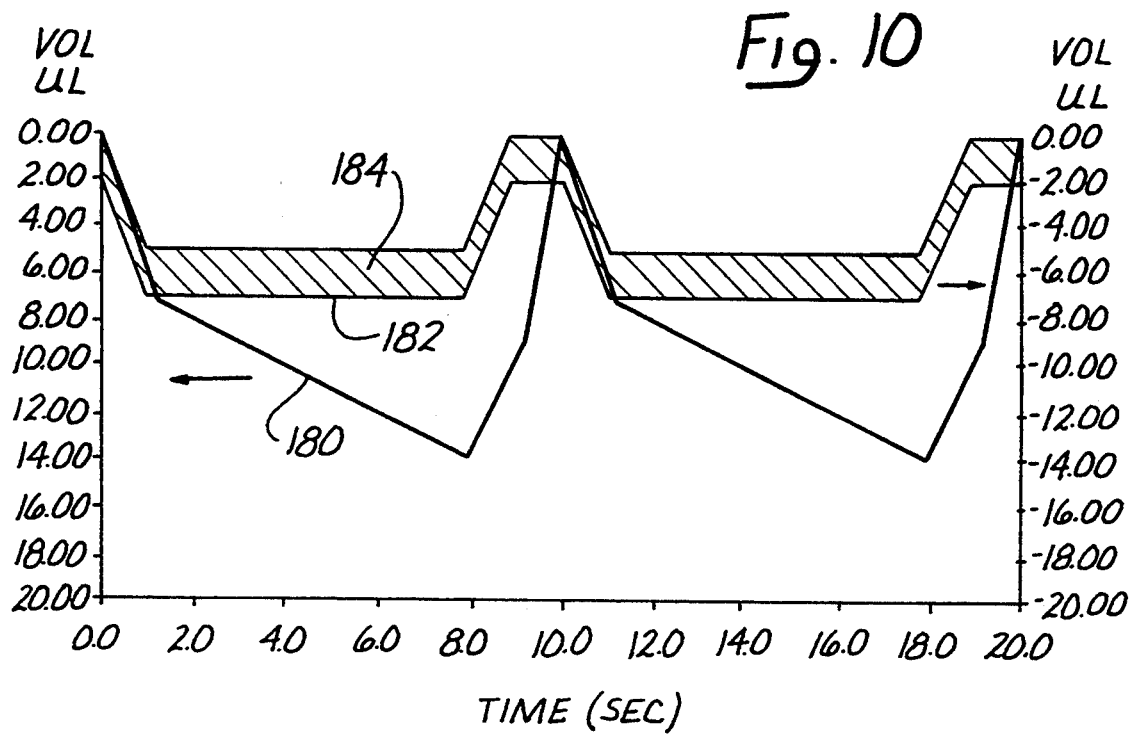
FIG. 10 is a schematic graphical illustration of the wave form in accordance with which the volume oscillator is activated.

The piston stem 125 is operated in accordance with a wave form shown graphically as 180 in FIG. 10. This wave form is expressed in terms of the volume (microliters or uL) of chamber 170 versus time. The flow of blood into and out of the lumen 61 is shown at 182. This is expressed in terms of volume (microliters or uL) versus time. The cross hatched portion 184 of FIG. 10 represents the interface zone 113. Thus, that area of FIG. 10 above portion 184 can be considered substantially exclusively blood, while that area below portion 184 can be considered substantially exclusively solution from source 19. Throughout the time the piston stem 125 is activated, sensors 69, 71 and 73 continuously provide parameter sensitive signals to instrument 17 indicative of the values of the respective parameters of interest.

As shown in FIG. 10, the piston stem 125 is initially moved relatively quickly to increase the volume of chamber 170 so as to expose the sensors 69, 71 and 73 to substantially exclusively blood. This is done by bringing into the lumen 61 only 5 uL of blood during the first second at a "safe" (from the standpoint of avoiding damage to the blood) velocity of 5 uL/second. For the next seven seconds, the piston stem 125 continues to move so as to maintain about 5 uL of substantially exclusively blood in lumen 61. During this time, the drip solution from source 19 is accommodated by a compensating expansion of the volume of chamber 170. After this period of time, the blood is expelled from lumen 61 at the "safe" velocity of 5 uL/second for the next second. Finally, the drip solution that was stored in chamber 170 is quickly expelled in the last second to give the sensor tip with a "fast flush". This 10 second cycle then repeats, as shown in FIG. 10. This cycle can be repeated continuously, intermittently or on demand, as desired and as imputed into the control module 179.

The values of the parameters of interest in the blood in the radial artery of the patient can be accurately determined from the average values provided by instrument 17 while volume oscillator 29 is active. This is done, as described above, by factoring out from these provided average values the contribution to such values obtained while the sensors 69, 71 and 73 are exposed to substantially exclusively the solution from source 19. To illustrate, assume that the average carbon dioxide concentration provided by instrument 17 while volume oscillator 29 is active is 40 mm Hg, and the carbon dioxide sensor 71 is exposed to substantially exclusively solution from source 19 (containing no carbon dioxide) for 20% of the cycle time of the volume oscillator. The carbon dioxide concentration in the blood in the radial artery of the patient, in mm Hg, is equal to $$\frac{40 - .2(0)}{.8} \text{ or 50 mm Hg.}$$

It has been found that this approach provides increased accuracy in measuring carbon dioxide concentrations and oxygen concentrations of about 90 mm of Hg. (partial pressure) or greater relative to, for example, a system in which the sensors are exposed to substantially exclusively blood and the interface zone 113 throughout the period during which parameter sensitive signals are provided to instrument 17.

In addition, the blood pressure monitored by pressure transducer 31 is substantially unaffected by the action of the volume oscillator 29, particularly during the above-noted seven second period. Further, because of the relatively smooth functioning of stepping motor 157, even with blood being moved into and out of lumen 61, the blood pressure measurements of pressure transducer 131 are relatively unaffected by the volume oscillator 29.

The above-noted cycle is repeated except that 10 uL of substantially exclusively blood is introduced into the lumen 61 instead of 5 uL of substantially exclusively blood, as described above. Comparable results are obtained.

The present system has been found to provide accurate and reliable determinations of the values of parameters of interest in blood. Such determination accuracy is quite unexpected since the sensors are preferably exposed to substantially exclusively a non-blood-containing fluid medium for a portion of the time the sensors provide parameters sensitive signals. Such determinations are provided in a relatively straight forward manner with little or no interference with other components, for example, the pressure transducer, of the present system. The risk of thrombus formation is reduced, for example, by introducing only a relatively small amount of blood into the lumen and/or by exposing the sensors to substantially exclusively a non-blood-containing fluid medium while the volume oscillator is inactive and/or by "fast flushing" the sensor tip when the volume oscillator is active. In addition, because the risk of thrombus formation is reduced, the present sensing system may be employed in vivo for a longer period of time, for example, on the order of about 72 hours or longer, relative to prior art systems where thrombus formation and other factors rapidly reduced system accuracy. In effect, the present system has enhanced biocompatibility. Further, the present volume oscillator system is preferably partially disposable so that the advantages of the present system can be achieved in a cost effective manner while maintaining patient safety and isolation.

While this invention has been described with respect to various specific examples and embodiments, it is to be understood that the invention is not limited thereto and that it can be variously practiced within the scope of the following claims.

What is claimed is:

1. An assembly for the sensing of a blood parameter comprising:
    a sensing element for sensing a parameter of blood and providing a signal in response thereto, and an elongated transmission member for transmitting said signal from said sensing element;
    a catheter having a proximal end, a distal end, and a lumen extending therethrough, said lumen having an opening in said distal end, said catheter being sized and adapted so that at least said distal end and said opening are receivable within a blood vessel of a patient, said sensing element being located within said lumen at a position away from said proximal end of said catheter and at least 4 mm proximal of said opening, said catheter being configured such that said catheter is capable of being connected to a flush solution source so as to allow for the introduction of flush solution into said lumen;
    a volume oscillator in fluid communication with said lumen, said volume oscillator being adapted to periodically cause blood from the blood vessel of the patient to move into and out of said lumen such that said sensing element is exposed to substantially exclusively blood for a portion of the time said volume oscillator is activated and to substantially exclusively said flush solution for another portion of the time said volume oscillator is activated; and
    means for calculating the value of said blood parameter based upon both the values sensed by said sensing element when exposed to substantially exclusively blood and when exposed to substantially exclusively said flush solution.

2. The assembly of claim 1 wherein said sensing element is located at least 6 mm proximal of said opening.

3. The assembly of claim 1 wherein said sensing element is located up to 40 mm proximal of said opening.

4. The assembly of claim 1 wherein said sensing element is located up to 20 mm proximal of said opening.

5. The assembly of claim 1 wherein said sensing element is located closer to said opening than to said proximal end of said catheter.

6. The assembly of claim 1 wherein said sensing element is adapted for sensing carbon dioxide.

7. The assembly of claim 1 wherein said catheter has a longitudinal axis and an average diameter within said lumen perpendicular to said longitudinal axis of about 0.56 mm or less.

8. The assembly of claim 1 wherein said volume oscillator is preprogrammed to periodically cause blood to enter said lumen and to exit said lumen in a predetermined time sequence.

9. The assembly of claim 1 wherein said volume oscillator includes a housing and a piston, which are adapted to be disposed of after use with a single patient, and an actuator adapted to be removably coupled to said piston.

10. The assembly of claim 1 wherein said sensing element is adapted for sensing oxygen.

11. An assembly for the sensing of a blood parameter comprising:
    a sensing element for sensing a parameter of blood and providing a signal in response thereto, and an elongated transmission member for transmitting said signal from said sensing element;
    a catheter having a proximal end, a distal end, and a lumen extending therethrough, said lumen having an opening in said distal end, said catheter being sized and adapted so that at least said distal end and said opening are receivable within a blood vessel of a patient, said sensing element being located within said lumen, said catheter being configured such that said catheter is capable of being connected to a flush solution source so as to allow for the introduction of flush solution into said lumen;
    a volume oscillator is fluid communication with said lumen, said volume oscillator being adapted to periodically cause blood from the blood vessel of the patient to move into and out of said lumen such that said sensing element is exposed to substantially exclusively blood for a portion of the time said volume oscillator is activated and to substantially exclusively said flush solution for another portion of the time said volume oscillator is activated; and
    means for calculating the value of said blood parameter based upon both the values sensed by said sensing element when exposed to substantially exclusively blood and when exposed to substantially exclusively said flush solution.

12. The assembly of claim 11 wherein said sensing element is located at least 10 mm distal of said proximal end of said catheter.

13. The assembly of claim 11 wherein said sensing element is adapted for sensing carbon dioxide.

14. The assembly of claim 12 wherein said sensing element is adapted for sensing oxygen.

15. A method of sensing a parameter of blood comprising:
providing a catheter having a proximal end, a distal end, and a lumen extending therethrough, said lumen having an opening in said distal end, at least said distal end and said opening being positioned within a blood vessel of a patient;
providing a sensing element for sensing a parameter of blood and providing a signal in response thereto and an elongated transmission member for transmitting said signal from said sensing element, said sensing element being located within said lumen at a position at least 4 mm proximal of said opening;
introducing a flush solution from a flush solution source into said lumen;
providing a volume oscillator which, when activated, moves blood from the blood vessel of the patient into and out of said lumen; and
obtaining said signal from said sensing element while said sensing element is exposed to substantially exclusively blood, wherein said obtaining step further comprises exposing said sensing element to substantially exclusively said flush solution for a portion of the time said volume oscillator is activated and obtaining said signal while said sensing element is exposed to substantially exclusively said flush solution.

16. The method of claim 15 wherein said obtaining step comprises exposing said sensing element to substantially exclusively blood for a major portion of the time said volume oscillator is activated.

17. The method of claim 15 further comprising the step of exposing said sensing element to substantially exclusively said flush solution when said volume oscillator is inactive, and further comprising the step of locating said sensing element at least 6 mm distal of said proximal end of said catheter.

18. The method of claim 15 wherein said obtaining step comprises obtaining said signal from said sensing element which senses carbon dioxide.

19. The method of claim 15 further comprising the step of preprogramming said volume oscillator to periodically cause blood to enter said lumen and to exit said lumen in a predetermined time sequence.

20. The method of claim 15 wherein said introducing step comprises including an anti-clotting component in said flush solution.

21. The method of claim 15 further comprising the step of activating said volume oscillator so as to cause blood to rapidly enter said lumen, to expose said sensing element to substantially exclusively blood for a relatively long period of time, and to cause blood to rapidly exit said lumen without substantially detrimentally effecting the blood.

22. The method of claim 15 wherein said introducing step further comprises introducing the flush solution into said lumen at an increased flow rate for a period of time after blood exits said lumen.

23. The method of claim 15 wherein said obtaining step comprises obtaining said signal from said sensing element which senses oxygen.

24. A method of sensing a parameter of blood comprising:
providing a catheter having a proximal end, a distal end, and a lumen extending therethrough, said lumen having an opening in said distal end, at least said distal end and said opening being positioned within a blood vessel of a patient;
providing a sensing element for sensing a parameter of blood and providing a signal in response thereto, and an elongated transmission member for transmitting said signal from said sensing element, said sensing element being located within said lumen;
introducing a flush solution from a flush solution source into said lumen;
providing a volume oscillator which, when activated, moves blood from the blood vessel of the patient into and out of said lumen so that said sensing element is exposed to substantially exclusively blood for a portion of the time said volume oscillator is activated and to substantially exclusively said flush solution for another portion of the time said volume oscillator is activated; and
obtaining said signal from said sensing element while said sensing element is exposed to substantially exclusively blood and while said sensing element is exposed to substantially exclusively said flush solution.

25. The method of claim 24 further comprising the step of exposing said sensing element to substantially exclusively said flush solution when said volume oscillator is inactive.

26. The method of claim 24 further comprising the step of activating said volume oscillator so as to expose said sensing element to substantially exclusively blood and to substantially exclusively said flush solution at predetermined times, and further comprising the step of calculating the value of said blood parameter using a known value of the parameter in said flush solution.

27. The method of claim 24 wherein said obtaining step comprises obtaining said signal from said sensing element which senses carbon dioxide.

28. The method of claim 24 further comprising the step of preprogramming said volume oscillator to periodically cause blood to enter said lumen and to exit said lumen in a predetermined time sequence.

29. The method of claim 24 wherein said introducing step comprises including an anti-clotting component in said flush solution.

30. The method of claim 24 further comprising the step of activating said volume oscillator so sensing element to substantially exclusively blood for a relatively long period of time, and to cause blood to rapidly exit said lumen without substantially detrimentally effecting the blood.

31. The method of claim 24 wherein said introducing step comprises introducing the flush solution into said lumen at an increased flow rate for a period of time after blood exits said lumen.

32. The method of claim 24 wherein said obtaining step comprises obtaining said signal from said sensing element which senses oxygen.

33. An assembly for the sensing of a blood parameter comprising:
a sensing element for sensing a parameter of blood and providing a signal in response thereto, and an elongated transmission member for transmitting said signal from said sensing element;

a catheter having a proximal end, a distal end, and a lumen extending therethrough, said lumen having an opening in said distal end, said catheter being sized and adapted so that at least said distal end and said opening are receivable within a blood vessel of a patient, said sensing element being located within said lumen; and a volume oscillator in fluid communication with said lumen, wherein said volume oscillator includes a housing and a piston, which are adapted to be disposed of after use with a single patient, and an actuator adapted to be removably coupled to said piston.

34. A method of sensing a parameter of blood comprising:

providing a catheter having a proximal end, a distal end, and a lumen extending therethrough, said lumen having an opening in said distal end, at least said distal end and said opening being positioned within a blood vessel of a patient;

providing a sensing element for sensing a parameter of blood and providing a signal in response thereto and an elongated transmission member for transmitting said signal from said sensing element, said sensing element being located within said lumen;

introducing a flush solution from a flush solution source into said lumen;

providing a volume oscillator which, when activated, moves blood from the blood vessel of the patient into and out of said lumen;

obtaining said signal from said sensing element while said sensing element is exposed to substantially exclusively blood; and exposing said sensing element to substantially exclusively said flush solution when said volume oscillator is inactive.

35. A method of sensing a parameter of blood comprising:

providing a catheter having a proximal end, a distal end, and a lumen extending therethrough, said lumen having an opening in said distal end, at least said distal end and said opening being positioned within a blood vessel of a patient;

providing a sensing element for sensing a parameter of blood and providing a signal in response thereto and an elongated transmission member for transmitting said signal from said sensing element, said sensing element being located within said lumen;

providing a volume oscillator which, when activated, moves blood from the blood vessel of the patient into and out of said lumen;

introducing a flush solution from a flush solution source into said lumen, wherein said introducing step further comprises introducing the flush solution into said lumen at an increased flow rate for a period of time after blood exits said lumen; and obtaining said signal from said sensing element while said sensing element is exposed to substantially exclusively blood.

* * * * *

UNITED STATES PATENT AND TRADEMARK OFFICE
CERTIFICATE OF CORRECTION

PATENT NO. : 5,335,658
DATED : August 9, 1994
INVENTOR(S) : William Bedingham

It is certified that error appears in the above-indentified patent and that said Letters Patent is hereby corrected as shown below:

Col. 16, line 55, claim 11, line 17, "is" should be --in--.

Col. 17, line 6, claim 14, line 1, "12" should be --11--.

Col. 17, lines 60-61, claim 21, lines 6-7, "effecting" should be --affecting--.

Col. 18, line 50, claim 30, line 2, after "so" insert --as to cause blood to rapidly enter said lumen, to expose said--.

Col. 18, line 54, claim 30, line 5, "effecting" should be --affecting--.

Signed and Sealed this

Twenty-seventh Day of December, 1994

Attest:

BRUCE LEHMAN

Attesting Officer      Commissioner of Patents and Trademarks